(12) United States Patent
Kenrick

(10) Patent No.: US 10,087,437 B2
(45) Date of Patent: Oct. 2, 2018

(54) METHOD FOR NUCLEI STORAGE

(71) Applicant: GE HEALTHCARE UK LIMITED, Buckinghamshire (GB)

(72) Inventor: Michael Kenneth Kenrick, Cardiff (GB)

(73) Assignee: GE HEALTHCARE UK LIMITED, Buckinghamshire (GB)

( * ) Notice: Subject to any disclaimer, the term of this patent is extended or adjusted under 35 U.S.C. 154(b) by 229 days.

(21) Appl. No.: 14/907,111

(22) PCT Filed: Jul. 23, 2014

(86) PCT No.: PCT/EP2014/065847
§ 371 (c)(1),
(2) Date: Jan. 22, 2016

(87) PCT Pub. No.: WO2015/011203
PCT Pub. Date: Jan. 29, 2015

(65) Prior Publication Data
US 2016/0152970 A1    Jun. 2, 2016

(30) Foreign Application Priority Data
Jul. 23, 2013 (GB) .................................. 1313146.1

(51) Int. Cl.
*C12N 15/10*    (2006.01)
(52) U.S. Cl.
CPC ..... *C12N 15/1006* (2013.01); *C12N 15/1003* (2013.01)

(58) Field of Classification Search
None
See application file for complete search history.

(56) References Cited

U.S. PATENT DOCUMENTS 5,985,327 A    11/1999    Burgoyne

FOREIGN PATENT DOCUMENTS

| EP | 0587951 A1 | 3/1994 |
|---|---|---|
| GB | 2355717 A | 5/2001 |
| WO | 200216383 | 2/2002 |
| WO | 2004033470 A2 | 4/2004 |

OTHER PUBLICATIONS

Great Britain Search Report dated Mar. 3, 2014 with was issued in connection with GB Patent Application No. 1313146.1 which was filed on Jul. 23, 2013.
International Search Report and Written Opinion dated Dec. 17, 2014 with was issued in connection with PCT Patent Application No. EP2014/065847 which was filed on Jule 23, 2014.
Seutin: "Preservation of avian blood and tissue samples for DNA analyses", Canadian Journal of Zoology vol. 69, No. 1, Jan. 1, 1991.

*Primary Examiner* — David C Thomas
(74) *Attorney, Agent, or Firm* — Eversheds Sutherland (US) LLP

(57) ABSTRACT

A method of performing data management in a high-speed data environment. The method includes collecting time-series information including multiple data types captured concurrently, and storing the collected time-series information in a process historian with organization, the organization occurring when the multiple data types are captured.

19 Claims, 2 Drawing Sheets

METHOD FOR NUCLEI STORAGE

FIELD OF INVENTION

Embodiments of the present invention relate to the field of nucleic acid storage, particularly to the long term storage of nuclei and recovery of nucleic acid. Embodiments of the invention provide methods and kits which can be used to capture and store nuclei at ambient temperatures and isolate nucleic acids by passive washing with a wash buffer. The invention has applications in the long term storage and easy processing of nucleic acids and is particularly useful in genotyping, diagnostics and forensics.

BACKGROUND TO THE INVENTION

Long-term storage, transport and archiving of nucleic acids on filter paper or chemically modified matrices is a well-known technique for preserving genetic material before the DNA or RNA is extracted and isolated in a form for use in genetic analysis such as the polymerase chain reaction (PCR). Thus, EP1563091 (Smith et al., Whatman) relates to methods for storing nucleic acids from samples such as cells or cell lysates. The nucleic acid is isolated and stored for extended periods of time, at room temperature and humidity, on a wide variety of filters and other types of solid support or solid phase media. Moreover, the document describes methods for storing nucleic acid-containing samples on a wide range of solid support matrices in tubes, columns, or multiwell plates.

WO/9003959 (Burgoyne) describes a cellulose-based solid support for the storage of DNA, including blood DNA, comprising a solid matrix having a compound or composition which protects against degradation of DNA incorporated into or absorbed on the matrix. This document also discloses methods for storage of DNA using the solid medium, and for recovery of or in situ use of DNA.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this method is that it eliminates the need for a separation step which is required for the removal of the lysis reagent.

GB2346370 (Cambridge Molecular Technologies Ltd) discloses a method involving applying a cellular sample containing nucleic acid to a filter, lysing the cells, then retaining the nucleic acid on the filter while removing contaminants.

WO9618731 (Deggerdal) describes a method of isolating nucleic acid whereby the sample is bound to a solid support and the sample is contacted with a detergent and subsequent steps performed to isolate the nucleic acid.

WO0053807 (Smith) discloses a medium for the storage and lysis of samples containing genetic material which can be eluted and analysed. The medium is coated with a lysis reagent and optionally with a weak base, a chelating agent, a surfactant or uric acid.

Ambient storage of biological samples is being seen as a better alternative to storage at low temperature. FTA™ (GE Healthcare) can be used for the storage of small sample sizes of approximately 100-200 ng of DNA. However there is a growing need for storage of larger sample volumes at ambient temperatures. A number of international prospective studies are recruiting many thousands of participants in an effort to investigate links between the living environment, life-style and genetics with the onset of disease. For example the EPIC prospective study on diet and cancer and the Canadian Partnership for Tomorrow Project. The studies rely on in-depth analysis of the participants at the outset and subsequent analysis of DNA following diagnosis of a significant life-threatening disease sometime in the future. Moderate blood volumes of 4 ml or more are required when conducting large cohort studies to allow genetic analysis of samples using contemporary and evolving techniques. Ideally samples should contain material that would allow additional investigation of other important molecules, for example long non-coding RNA. Therefore there is a need for a means to store large volumes of cell nuclei, which contains DNA, RNA and numerous other proteins, at ambient temperatures for current and future analytical studies.

Previous nuclei capture devices have included Nuclitip (GE Healthcare; described in U.S. Pat. No. 5,447,864, Kenrick et al.). The device consists of a microfilament weave of the tip of a pipette that processes up to 10 ml of fresh blood. The blood undergoes controlled lysis; the cell membrane is lysed leaving the majority of nuclei membrane intact. A planar treated membrane is located on the exterior of the Nuclitip pipette tip completely covering the tip's aperture such that the sample is filtered before entry into the tip and any DNA and nuclei present in the sample binds to the filter. The pipette tip is then washed with phosphate buffered saline (PBS) to remove any contaminants. U.S. Pat. No. 5,447,864 describes the method of separating cell components of cells using the nuclitip method and the possibility of storing the nuclei for longer periods on the membrane at −20° C. or below and for short periods if kept at 4° C. However the document does not disclose or suggest the long term storage of cell nuclei at ambient temperatures. In addition the document suggests the use of standard nucleic acid extraction techniques including the use of detergents to lyse the nuclear membrane.

There is therefore a need for an improved and simplified process for capturing and storing large quantities of nucleic acid, including DNA and RNA, at ambient temperature. The present invention addresses this problem and provides methods and kits which can be used for single step storage and extraction of nucleic acid from solid supports, particularly cellulose-derived supports.

SUMMARY OF THE INVENTION

According to a first aspect of the present invention, there is provided a method for storing cell nuclei comprising, selectively lysing the cytoplasmic membranes and a small proportion of the nuclear membranes present in a cellular sample to leave a large proportion of the cell nuclei intact, collecting the cellular sample on a solid support, washing the solid support, and storing the intact nuclei on the solid support at ambient temperature.

The intact nuclei may be stored at ambient temperature for a period of 1 day, 1 week, 1 month, 2 months, 6 months, 12 months, 1 year, 2 years, 5 years, 10 years, 15 years or 20 years.

In one aspect, the intact nuclei contain nucleic acid such as DNA or RNA.

In another aspect, the method additionally comprises the step of submerging the solid support in an organic solvent after washing the solid support and prior to storing the intact nuclei on the solid support at ambient temperature. Suitable organic solvents include, but are not limited to, alcohols such as ethanol or isopropanol.

In a further aspect, the solid support is air dried prior to storing the intact nuclei on the solid support at ambient temperature.

In one aspect, the lysis reagent is added to the solid support and subsequently dried in situ to preserve the nucleic acid.

In another aspect, the lysis reagent comprises an anionic surfactant or detergent. Examples of anionic surfactants include sodium dodecyl sulfate (SDS), ammonium dodecyl sulfate, sodium laureth sulfate, sodium lauroyl sarcosinate, sodium myreth, sulfate and sodium stearate.

In a further aspect, the cellular sample has a volume greater than 1 ml. Optionally, the cellular sample may have a volume greater than 5 ml. Optionally, the cellular sample may have a volume greater than 10 ml.

In one aspect, the solid support is a permeable membrane.

In another aspect, the solid support is selected from the group consisting of polyester membrane, polyamide membrane, polycarbonate membrane and cellulose membrane.

In a further aspect, the solid support is a polyester membrane.

In one aspect, the solid support is attached to a pipette tip. In this aspect, the solid support may be a polyester membrane.

In another aspect, the pipette tip is a Nuclitip.

In a further aspect, the method comprises the additional step of recovering the nucleic acid from the nuclei, for example by lysing the nuclei on the membrane.

In one aspect, the membrane undergoes passive washing with a wash buffer.

In another aspect, the nucleic acid is recovered by centrifugation.

In a further aspect, washing the solid support is performed by passing a washing fluid through the solid support.

According to a second aspect of the present invention, there is provided a kit for storing cell nuclei at ambient temperature comprising a solid support, and instructions for carrying out a method as hereinbefore described. The kit may optionally comprise a lysis reagent to lyse the cytoplasmic and nuclear membranes.

DETAILED DESCRIPTION OF THE INVENTION

Definitions

Figure 1:
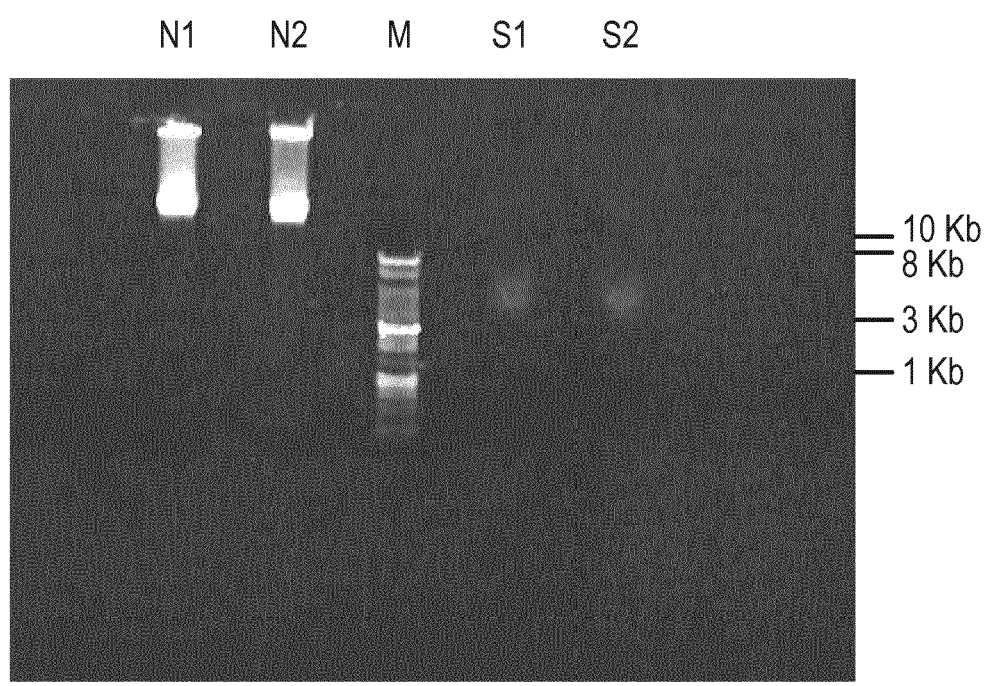
FIG. 1 shows N1 and N2 are high molecular weight DNA recovered from the Nuclitip by brief spinning in a microcentrifuge, M is DNA molecular weight markers and S1 and S2 are solutions removed from above each Nuclitip membrane after protease digestion and before gentle washing. Note very little nucleic acid-ethidium bromide fluorescence is seen in S1 and S2 demonstrating retention of high molecular weight DNA on the membrane during digestion. Gentle washing is effective and does not dislodge retained DNA. A short high speed spin in a microcentrifuge is effective at removing viscous high molecular weight DNA and shown in lanes N1 and N2.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, the word "Storing" is used to describe the process of maintaining or preserving the nucleic acid in a stable condition.

The term "Lysing" is used herein to describe the process of rupturing, denaturing or puncturing a structure, such as a cellular or sub-cellular membrane, including a nuclear membrane.

As used herein, the term "Cellular Sample" is used herein to refer to a fluid sample containing cellular material. The cellular material may originate from any suitable eukaryotic organism which contains nuclei, such as human, animal, plant, avian, insect and fish. The cellular material may for example be blood, saliva, urine, plasma.

As used herein, the term "Ambient temperature" means a temperature in the range of 10° C. to 30° C., particularly 15° C. to 26° C., more particularly, 18° C. to 23° C.

The term "Solid Support" as used herein includes but is not limited to cellulose-based products, cellulose, cellulose acetate, glass fibres, polyester, polyamide and polycarbonate or any combination thereof. A solid support of embodiments of the present invention may be porous.

"Nucleic Acid" as used herein refers to all forms of RNA (e.g. mRNA) and DNA (e.g. genomic DNA), as well as recombinant RNA and DNA molecules or analogues of DNA or RNA generating using nucleotide analogues, or mixtures thereof. The nucleic acid molecules can be single stranded or double stranded.

Chemicals and Materials Used

A list of the chemicals and their sources is given below:

Human Whole Blood collected in EDTA tubes (Tissue Solutions Ltd).

Sucrose/triton red cell lysis buffer (100 ml) was prepared by combining the ingredients listed below and made up to 100 ml with sterile distilled water:

Sucrose (Sigma, 57903)—11.0 g 10 mM Tris pH 8.0 (10 ml/L of 1 M stock) (Sigma, T3038)—1 ml 5 mM $MgCl_2$ (1.02 g/L $MgCl_2$ $6H_2O$) (Merck, 1.05833)—100 mg 1% (w/v) Triton x-100 (10 g/L) (Sigma, T9284)—1 g;

Phosphate Buffered Saline (PAA, H15-002);

Nuclitips (GE Healthcare);

Illustra Tissue and Cells GenomicPrep mini spin kit (GE Healthcare, 28-9042-74); Tris EDTA buffer: 10 mM Tris pH8.0 and 1.0 mM EDTA (Sigma, T9285-100 ml); 0.8% agarose/TAE gel (Affymetrix, part #75817); Ethidium bromide (Sigma, E1510); Control genomic DNA (Roche, 11691112001); Hind III and Bam H1 restriction endonucleases with respective restriction buffers (New England Biolabs, R0104T and R0136T); The following experimental results and examples are offered by way of illustration and not by way of limitation:

EXAMPLES

DNA Measurement from Nuclitips Using Gel Electrophoresis 2 ml of blood was collected and added to an equal amount of red cell lysis buffer. The sample was swirled and mixed end-over-end for a brief period and left on the bench for 3 minutes. Multiple nuclitips were used to collect the sample and capture the nuclei. Blood was collected until occlusion of the polyester membrane was evident by a slowing of the aspiration and expiration of the lysed blood when pumped back and forth across the membrane.

The plunger of the pipette was held down and the tip was washed sequentially in fresh phosphate-buffered saline by pumping the fluid back and forth across the membrane until the membrane was substantially free of haem.

The wash fluid was expelled and the tips were removed from the pipette and spun briefly in a bench-top microcentrifuge (1200 rpm, approximately 7 cm radius) for 10 seconds to remove residual fluid. The tips were then placed in a desiccator cabinet overnight for further drying.

The following day 3 dry tips containing the nuclei were each stored directly in a 1.5 ml microcentrifuge tube and 3 other tips were treated with 100 ul of absolute ethanol pipetted directly on the membrane. The tube lids were closed and the tubes were kept in a laboratory cupboard at ambient temperature (between approximately 15° C.-25° C.) for 60 days.

Processing Samples Following Long Term Storage Of The Nuclitips.

The ethanol was removed from the ethanol immersed tip by decanting and pulse spinning to dry the membrane.

Lysis Solution I from the Illustra Tissue and Cells GenomicPrep mini spin kit was used to lyse, digest and remove the genomic DNA from the membrane-trapped dried nuclei of both the ethanol treated tips and the dry treated tips.

Lyophilised proteinase K (3 mg) was dissolved in 1.5 ml sterile distilled water to prepare a 20 mg/ml solution of protease from which 20 ul was added to 100 ul of lysis 1 buffer. 50 ul of the protease containing lysis buffer was pipetted directly onto the dry membrane of the Nuclitips. The tubes were then closed and placed in a 55° C. water bath for 30 minutes.

The tubes were then opened and approximately 300 µl of TE$^{-1}$ buffer was added down the sides of the tubes and inside the barrel of the tip to wash away the lysis buffer and digested peptides. The tubes remained on the bench for 2 minutes before decanting the wash solution. This process was repeated twice before adding 50 µl of TE$^{-1}$ buffer to each tube and spinning in a microcentrifuge at maximum speed (12,000 rpm) for 1 minute to collect genomic DNA.

The recovered DNA solution from each device was approximately 70 µl of clear, colourless and highly viscous solution. The solution above the membrane following digestion was aspirated and kept before the addition of the first wash solution. The solution was run on a 0.8% agarose/TAE gel alongside a sample of the recovered gDNA sample and stained with ethidium bromide (FIG. 1). Very little staining of nucleic acid was detected for sample S1 and sample S2 with very little release of nucleic acid from the membrane during proteolysis. Following gentle washing, purified high molecular weight DNA could be recovered by a short high speed spin in a microcentrifuge and that the described method was effective at collecting the majority of the nucleic acid from the membrane as shown by the high ethidium bromide fluorescence on the gel for N1 and N2.

To determine the concentration and quality of the DNA, a small sample was removed from each tube following prolonged vortexting (to overcome viscosity) and read of a NanoVue Plus spectrophotometer. The results are present in table 1 below and demonstrate the high quality and concentration of nucleic acid present. The concentration of genomic DNA for N1 was 134 ng/ul and 86 ng/ul for N2.

TABLE 1

| Enzymatic Digestion Of Genomic DNA Recovered From Dry Stored Nuclei. | | | | |
|---|---|---|---|---|
| Sample | A260 | A280 | A260/280 | Total yield |
| N1 | 3.06 | 1.75 | 1.72 | 9.4 ug |
| N2 | 2.23 | 1.33 | 1.82 | 6.0 ug |

Figure 2:
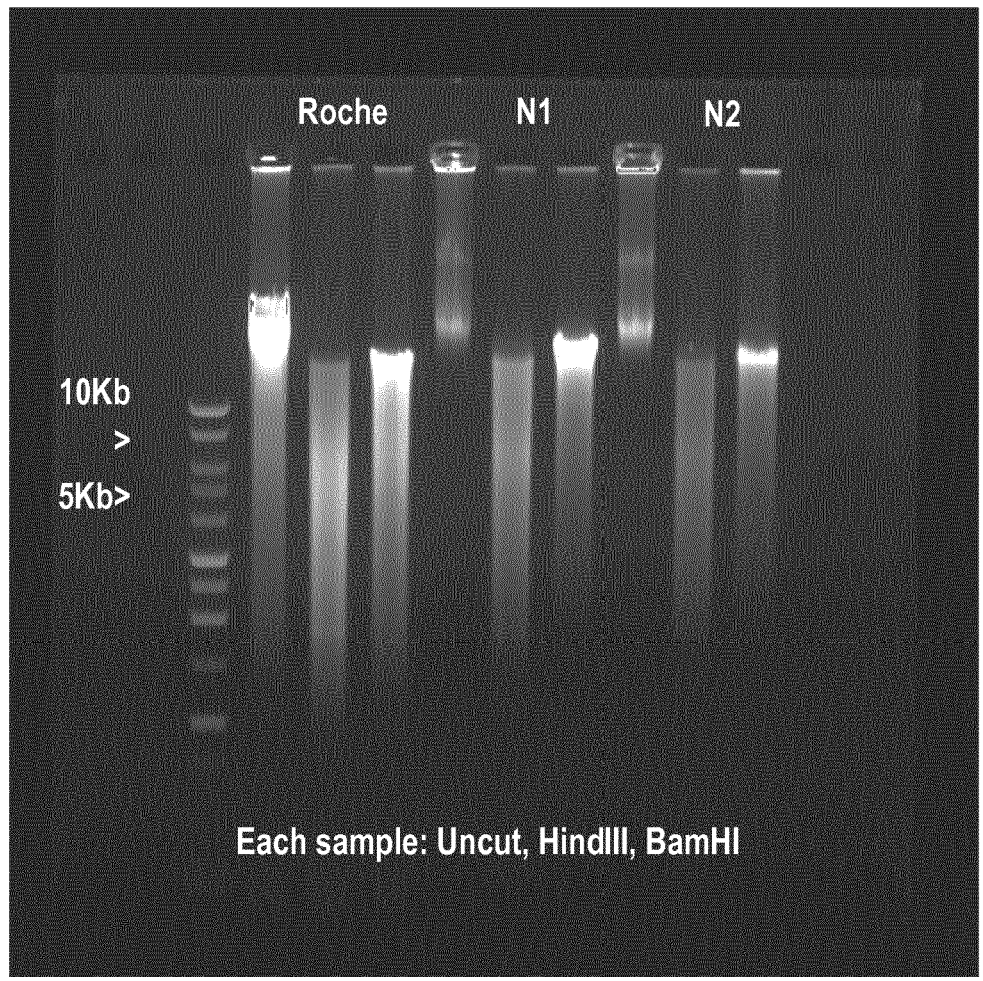
FIG. 2 shows the results from both N1 and N2 DNA samples processed using the nuclitip method described in an embodiment of the present invention. The image shows uncut DNA, Hind III and BamH1 digested Roche control DNA, N1 and N2 samples. The results presented demonstrate it is possible to store enriched concentrated nuclei at room temperature without detriment to the genomic sample.

10 ul of each sample N1(1.5 ug) and N2(1 ug) and control sample Roche DNA (2 ug) was digested with either 40 units of a BamH1 or Hind III endonucleases in a total volume of 20 ul and stored at 37° C. for 3 hours. The cut and uncut DNA was run on a 0.8% agarose/TAE gel against known molecular weight DNA markers and stained with ethidium bromide as seen in FIG. 2. The results presented demonstrate it is possible to store enriched concentrated nuclei at room temperature without detriment to the genomic sample. The developed process is able to produce high quality, high molecular weight genomic DNA with a concentration above 50 ng/ul, having an absorbance ratio of A260:A280 close to 1.8 and suitable for downstream manipulations like restriction endonuclease digestion.

While preferred illustrative embodiments of the present invention are described, one skilled in the art will appreciate that the present invention can be practised by other than the described embodiments, which are presented for the purposes of illustration only and not by way of limitation. The present invention is limited only by the claims that follow.

The invention claimed is:

1. A method for storing cell nuclei comprising:
   selectively lysing the cytoplasmic membranes and a minority proportion of the nuclear membranes present in a cellular sample to leave a majority proportion of the cell nuclei intact,
   collecting the cellular sample on a solid support,
   washing the solid support, and
   storing the intact nuclei on the solid support at ambient temperature.

2. The method according to claim 1, wherein the intact nuclei contains nucleic acid.

3. The method according to claim 1, further comprising submerging the solid support in an organic solvent after washing the solid support and prior to storing the intact nuclei on the solid support at ambient temperature.

4. The method according to claim 1, wherein the solid support is air dried prior to storing the intact nuclei on the solid support at ambient temperature.

5. The method according to claim 2, wherein a lysis reagent is added to the solid support and subsequently dried in situ to preserve the nucleic acid.

6. The method according to claim 5, wherein the lysis reagent comprises an anionic surfactant or detergent.

7. The method according to claim 6, wherein the anionic surfactant is sodium dodecyl sulfate (SDS).

8. The method according to claim 1, wherein the cellular sample has a volume greater than 1 ml.

9. The method according to claim 1, wherein the cellular sample has a volume greater than 5 ml.

10. The method according to claim 1, wherein the cellular sample has a volume greater than 10 ml.

11. The method according to claim 1, wherein the solid support is a permeable membrane.

12. The method according to claim 1, wherein the solid support is selected from the group consisting of polyester membrane, polyamide membrane, polycarbonate membrane and cellulose membrane.

13. The method according to claim 1, wherein the solid support is a polyester membrane.

14. The method according to claim 1, wherein the solid support is attached to a pipette tip.

15. The method according to claim 14, wherein the solid support is a polyester membrane.

16. The method according to claim 14, wherein the pipette tip comprises a microfilament weave.

17. The method according to claim 2, further comprising recovering the nucleic acid from the nuclei after storing the intact nuclei on the solid support at ambient temperature.

18. The method according to claim 17, wherein the nucleic acid is recovered by lysing the nuclei on the membrane.

19. The method according to claim 18, wherein the membrane undergoes passive washing with a wash buffer.

* * * * *